United States Patent
Butler et al.

[11] Patent Number: 5,850,659
[45] Date of Patent: Dec. 22, 1998

[54] TOOTHBRUSH WITH BENDABLE HEAD

[75] Inventors: C. P. Butler, Lithonia, Ga.; F. M. Butler, Jr., Del Ray Beach, Fla.

[73] Assignee: The Smart Brush Corporation, Grayson, Ga.

[21] Appl. No.: 684,292

[22] Filed: Jul. 18, 1996

Related U.S. Application Data

[63] Continuation-in-part of Ser. No. 622,697, Mar. 26, 1996, Pat. No. 5,749,381.

Related U.S. Application Data

[60] Provisional application No. 60/011,896 Feb. 20, 1996.
[51] Int. Cl.$^6$ .............................. A46B 7/04; A46B 9/04
[52] U.S. Cl. ..................... 15/167.1; 15/172; 15/176.1; 15/201
[58] Field of Search ................ 15/176.1, 176.2, 15/176.3, 176.6, 172, 201, 145, 167.1, 187, 186, 160

[56] References Cited

U.S. PATENT DOCUMENTS

| | | | |
|---|---|---|---|
| 490,831 | 1/1893 | Lohers | 15/172 |
| 1,702,042 | 2/1929 | Doskow | 15/176.6 |
| 2,003,243 | 5/1935 | Campbell et al. | 15/172 |
| 2,016,153 | 10/1935 | McWhirter | 15/176.2 |
| 2,418,344 | 4/1947 | Goldberg | 15/176.1 |
| 3,081,783 | 3/1963 | Miller | 15/176.1 |
| 4,829,621 | 5/1989 | Phenegar | 15/172 |
| 4,991,249 | 2/1991 | Suroff | 15/176.2 |
| 5,010,906 | 4/1991 | Preciutti | 15/167.1 |
| 5,072,477 | 12/1991 | Pai | 15/176.6 |
| 5,323,504 | 6/1994 | McCusker | 15/172 |
| 5,694,658 | 12/1997 | Huang et al. | 15/172 |

*Primary Examiner*—Gary K. Graham
*Attorney, Agent, or Firm*—Deveau, Colton & Marquis

[57] ABSTRACT

An ergonomically designed toothbrush having an oversized handle, a shapeable stem, interchangeable, flexible heads of different sizes, bristles arrangements, and geometrical configurations. The handle is generally cylindrical in shape so as to readily fit in the palm of ones hand while having a flattened portion against which the thumb and fingertips may be rested. The handle has attached thereto a rotation means which may be selectively set in a variety of positions about the longitudinal axis of the handle. When a stem with a flexible toothbrush head is attached to the rotation means, the user of the toothbrush may bend the head and set the orientation of the bristles on the head such that they are at a 45° relative to the surface of the teeth while the flat portion of the handle is generally parallel to the surface of the teeth so that the Bass brushing technique may be implemented while moving the toothbrush back and forth in short strokes in a conventional manner and so that all teeth may be effectively reached and brushed regardless of the contour of one's teeth and mouth.

12 Claims, 4 Drawing Sheets

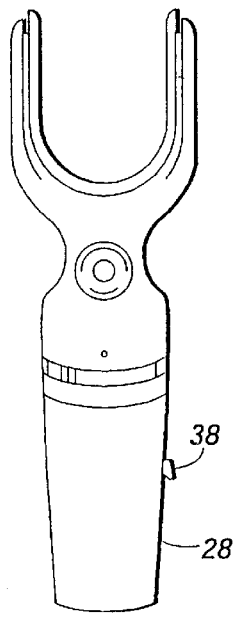
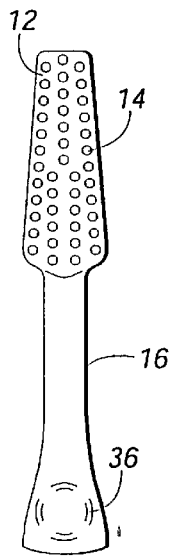
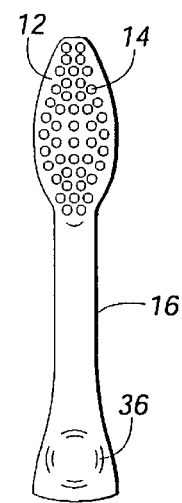
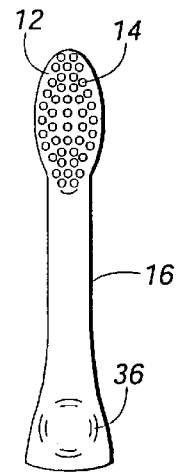
FIG. 5a  FIG. 5b  FIG. 5c  FIG. 5d
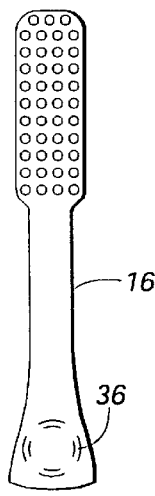
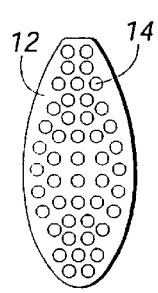
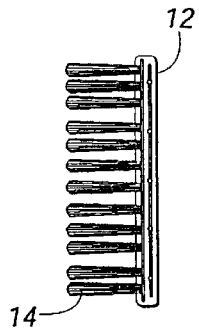
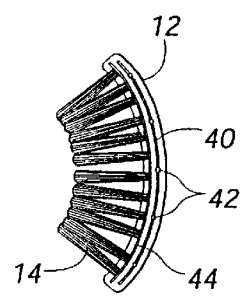
FIG. 5e  FIG. 6a  FIG. 6b  FIG. 6c

TOOTHBRUSH WITH BENDABLE HEAD

This is a continuation-in-part of application Ser. No. 08/622,697 filed on Mar. 26, 1996, now U.S. Pat. No. 5,749,381 which is a provisional application Ser. No. 60/011,896 filed Feb. 20, 1996.

BACKGROUND OF THE INVENTION

1. Field of the Invention

This invention relates generally to toothbrushes and more particularly is directed to a toothbrush with interchangeable, bendable heads which may be flexed and/or rotated about the axis of the handle so that the head of the toothbrush is positioned at an optimum angle relative to the surface of the teeth and gums.

2. Description of the Prior Art

The Bass technique of brushing teeth is widely recommended by the American Dental Association for removal of plaque which accumulates on the surface of the teeth and in the sulcus, i.e., the tooth surface which is hidden by the gums. Basically, this technique involves holding a standard toothbrush at about a 45° angle relative to the surface of the teeth such that a portion of the bristles clean the teeth while another portion of the bristles clean the gums as the toothbrush is moved back and forth in short strokes. Implementation of this technique with a standard toothbrush requires that the user of the toothbrush rotate his or her wrist at about a 45° angle while at the same time using the short back and forth strokes required by the Bass technique on both the front and back surfaces of the teeth, both the top and bottom sets. Holding ones wrist in this unnatural position while brushing for the time period recommended by dental professionals can be quite tiring particularly for children and individuals with arthritis. Often these individuals do not have the necessary manual dexterity or stamina to effectively practice the Bass brushing technique. Therefore, a need exists for a toothbrush which facilitates use of the Bass brushing technique while not imposing unnecessary burdens on the user of the toothbrush such as hand and wrist fatigue which discourage proper brushing technique and encourage reversion to less effective brushing techniques. Thus, there is a need for a toothbrush which allows one to easily implement the Bass brushing technique. It is to the provision of such a toothbrush that the present invention is primarily directed.

Another short coming of standard toothbrushes relates to failure of the toothbrush user to follow dental professionals' recommendation that the toothbrush bristles be completely dried between uses. This recommendation is at odds with the recommendation that brushing take place after each meal, particularly if only one toothbrush is used. For example, if one eats breakfast at about eight o'clock and brushes his or her teeth thereafter, it is unlikely that the toothbrush bristles will be dry by one o'clock or so after he or she has had lunch unless the toothbrush is stored at an elevated temperature or a specific drying means is utilized. Thus, there is a need for a system of oral hygiene which permits one to utilize a toothbrush wherein the bristles are dried between subsequent uses.

BRIEF SUMMARY OF THE INVENTION

The present invention is a toothbrush for easily implementing the Bass brushing technique. The toothbrush has a generally cylindrical handle which is oversized to enhance manual dexterity and to make gripping of the handle more comfortable for the user. The generally cylindrical handle has a flattened portion along its length against which the thumb and fingertips may be rested so as to firmly hold the handle at a fixed angle while brushing. Connected to the handle is a rotation means to which a variety of interchangeable stems may be connected, all of which have a head of a different size, bristle arrangement, or geometrical configuration. The rotation means is adapted so that it may be selectively positioned at one of a plurality of locations about the longitudinal axis of the handle. With such an arrangement, the Bass brushing technique may be implemented by attaching a stem with a preferred head shape to the rotation means and adjusting the rotation means so that the bristles are aligned at a 45° angle relative to the surface of the teeth while the flat portion of the handle is generally parallel to the surface of the teeth. A significant achievement of the present invention is provided by multiple raised sections or grips on both the flat portion and the generally cylindrical portions of the handle which permit the user of the toothbrush to brush all dental surfaces while maintaining the same grip on the handle and simply adjusting the rotational angle of the head. In addition, the stem and head are bendable so that they may be repositioned to obtain the most effective alignment and brushing angles for the particular user of the toothbrush.

Optionally, the head connected to the stem may be replaced with a dental floss holding device for storing dental floss and for mounting a length of dental floss thereon allowing one to floss the areas between teeth. Also, the handle of the toothbrush may be formed of a rubberized material which is slightly depressed when force is applied thereto so as to reduce hand and wrist fatigue when brushing. A ventilated storage container for drying toothbrush bristles in a protected environment may also be provided.

Thus, it is an object of the present invention to provide a toothbrush having a construction which facilitates implementation of the Bass brushing technique.

It is another object of the present invention to provide a toothbrush having interchangeable heads so that heads having a variety of sizes, shapes, bristle arrangements and geometrical configurations may be used.

It is another object of the present invention to provide a toothbrush which may be converted for use as a device for flossing.

It is yet another object of the present invention to provide a toothbrush having a handle which is ergonomically designed to reduce wrist and hand fatigue while brushing.

Yet another object of the present invention is to provide an oral hygiene system allowing for interchangeable toothbrush heads of different configurations which, when used over a period of time, insure that all surfaces of the teeth are cleaned during brushing.

Still another object of the present invention is to provide an oral hygiene system which allows for adequate drying of toothbrush bristles between subsequent uses.

A further object of the present invention is to provide a complete oral care system that includes means for flossing teeth.

These objects, and other objects, features and advantages of the present invention will become more apparent to one skilled in the art when the following detailed description of the preferred embodiment is read in conjunction with the appended drawings in which like reference numerals designate like parts throughout the several views.

BRIEF DESCRIPTION OF THE DRAWINGS

FIGS. 2b–2c are front views of the toothbrush of FIG. 2a showing the head rotated 45 degrees from the position depicted in FIG. 2a.

FIG. 4 is a front view of the handle of the toothbrush depicted in FIG. 2a.

FIGS. 5a–5e are front views of preferred attachments for the toothbrush handle depicted in FIG. 4.

FIG. 6a is a front view of a preferred embodiment of the bendable toothbrush head of the present invention.

FIGS. 6b and 6c are side views of the bendable toothbrush head depicted in FIG. 6a.

DETAILED DESCRIPTION OF THE PREFERRED EMBODIMENTS

The present invention is a toothbrush for implementing the method of brushing teeth which is recommended by the American Dental Association (ADA), i.e., the Bass brushing technique. This technique has been shown to be most effective in removing plaque and food particles from the inner, outer, and biting surfaces of teeth as well as the gingival margin. The technique involves holding a toothbrush at approximately a forty-five (45) degree angle relative to the surface of the teeth with about half the bristles touching the teeth and the other half touching the gums while gently moving the toothbrush back and forth in short (half-a-tooth-wide) strokes.

Figure 1:
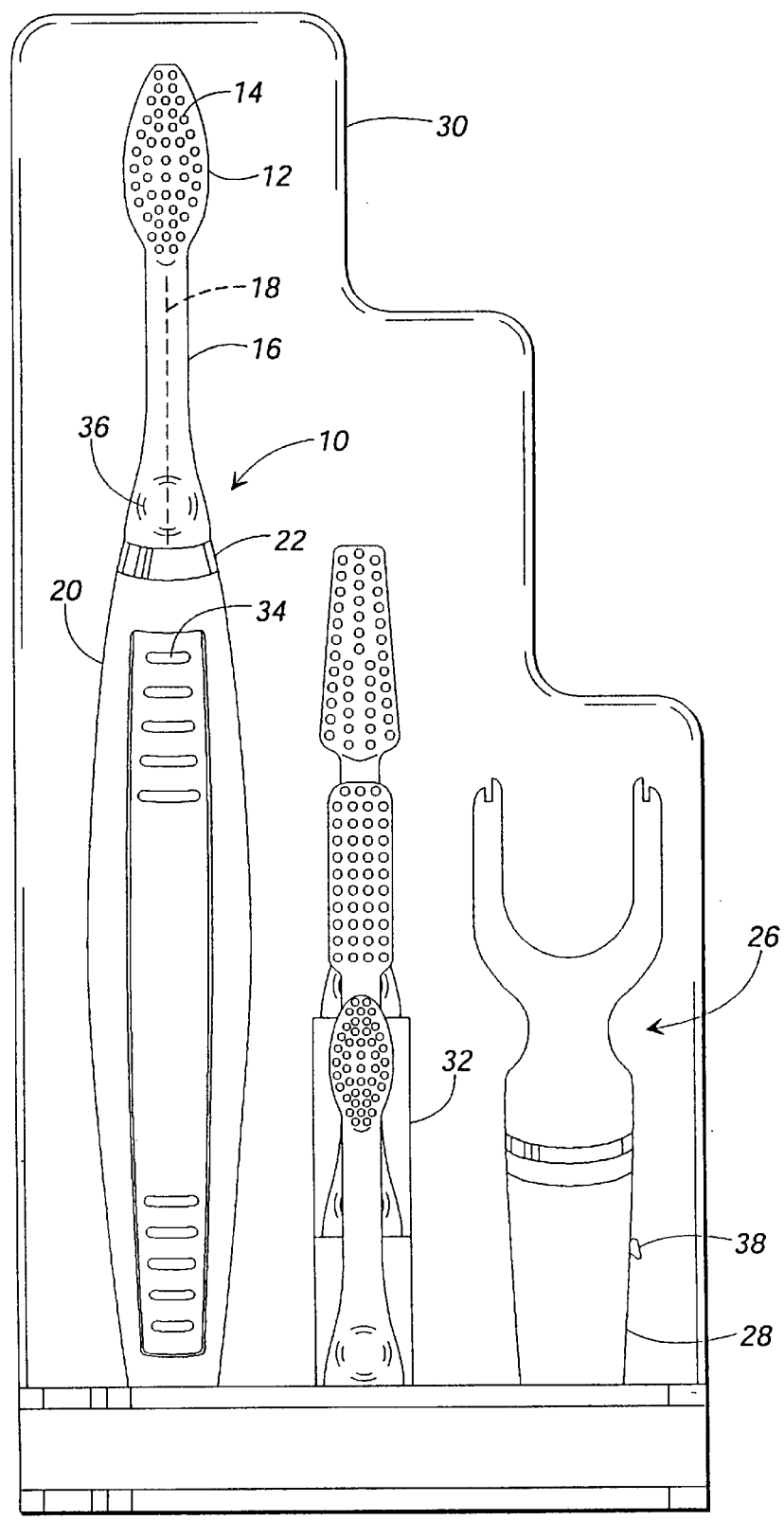
FIG. 1 is a front view of the oral hygiene system of the present invention including toothbrush handle, interchangeable heads, dental floss holder, and a preferred storage and drying container.

Referring now to the drawings, FIG. 1 shows the complete oral care system of the present invention mounted in a transparent storage container 30 having a plurality of apertures (not shown) therein for ventilation. The storage container 30 provides a convenient means of drying toothbrush bristles and guards against bacterial contamination which frequently occurs when a toothbrush is simply placed on a countertop. The base of the storage container 30 may be provided with appropriately shaped notches (not shown) and shelves 32 to accommodate the bottom portions of the various components of the oral care system.

Figure 3:
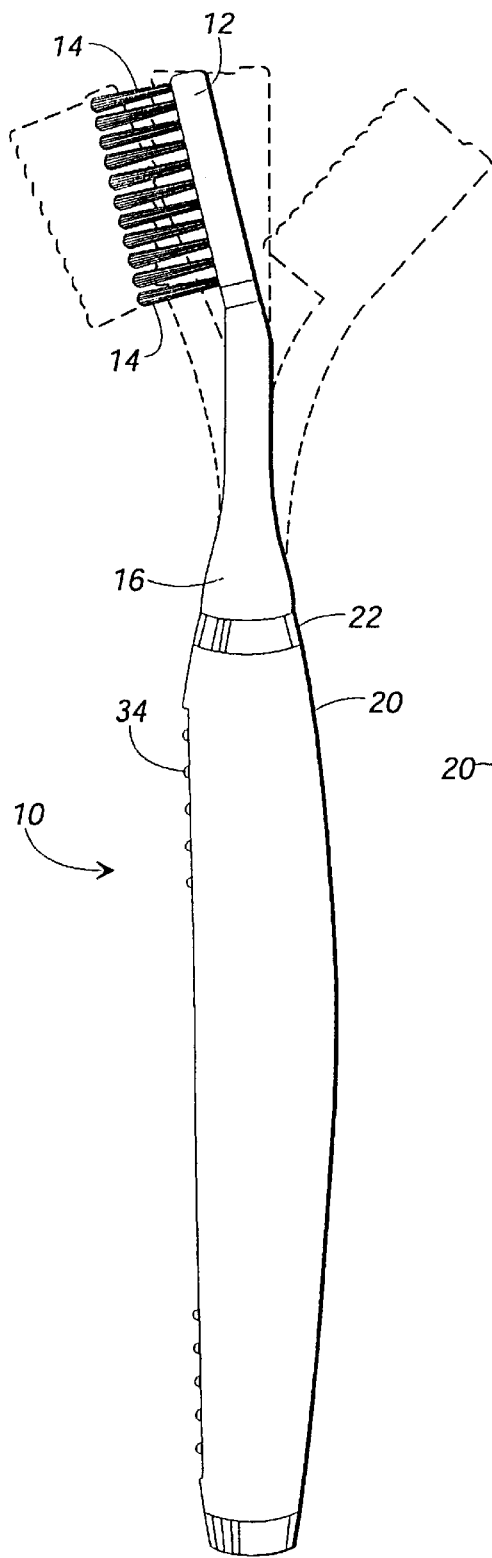
FIG. 3 is a side view of the toothbrush of FIG. 2a demonstrating various static positions in which the stem may be placed.
Figure 4:
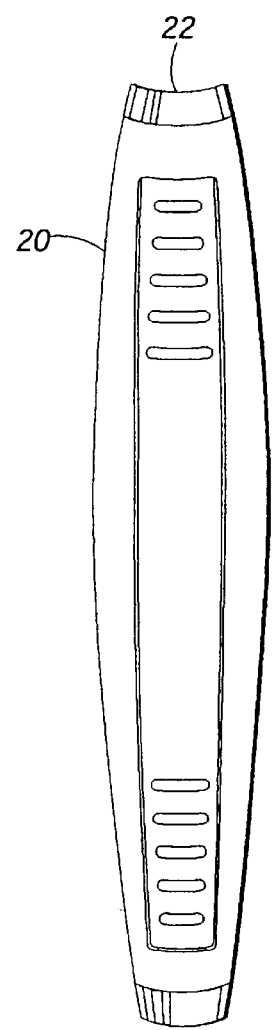

The oral care system includes a padded handle 20 which has a larger diameter than the standard, commercially available toothbrush which makes the handle 20 more comfortable and easier to use because less force is required to stably hold the handle 20. Also, the larger handle 20 requires less rotational turning about the longitudinal axis of the handle 20 than is required by a smaller handle to achieve the same result. The handle 20 is generally cylindrical in shape having a cross section which is predominantly circular (about one inch in diameter) except for a generally flat portion defined by a chord of the circular cross section of the handle. As better shown in FIG. 3, the generally flat portion extends along almost the entire length of the handle 20 and provides a convenient surface against which one's thumb and fingertips may be placed while brushing. The handle 20 is preferably formed of a "squeezable" material which deflects slightly when a gripping force is applied. Such a construction makes the toothbrush 10 more comfortable to hold and therefore easier to use. Optionally, the toothbrush of the present invention may be formed with a flat portion and grips on both the front and back (not shown) of the handle to aid in more firmly grasping the handle, particularly when the handle is wet. In the "double-sided" configuration one is enabled to implement the Bass brushing technique in all quadrants of the mouth while maintaining the same grip on the handle. The grips 34 may be arranged either vertically or horizontally as depicted in FIG. 3. The provision of multiple raised sections or grips 34 on both the front and back of the handle 20 permit the user of the toothbrush 10 to brush all dental surfaces while maintaining the same grip on the handle 20 by simply adjusting the rotational angle of the head 12 to a 45 degree angle relative to the surface of the teeth and gums.

Attached to the top portion of the handle 10 is a rotating disk 22 which is designed to detachably receive various attachments having teeth cleaning implements such as a toothbrush head or dental floss holder formed at the end of a support stem. The rotating disk preferably has a fixed portion which is secured to the handle 20 and a rotating portion designed to be turned 360 degrees in either a clockwise or counterclockwise direction so that in one position, a stem 16 may be placed in the rotating disk so that the plane defined by the tips of the tufts of bristles 14 on the head 12 is generally parallel to the flat portion of the handle. The fixed portion 21 of rotating disk 22 is defined by the upper perimeter surface of handle 10, and the rotating portion 23 of rotating disk 22 is defined by the bottom perimeter contact surface of stem 16 when stem 16 and handle 10 are snapped together. That is, stem 16 rotates against rotating disk 22. In the preferred embodiment, the head 12 may be rotated in 45 degree increments. However, it will be clear to those skilled in the art that other angular increments may be utilized while still permitting implementation of the Bass brushing technique. For example, 1 degree or 15 degree increments may be used. With such an arrangement, the toothbrush head 12 can easily be used to carry out the Bass brushing technique by rotating the head 12 so that the bristles 14 are at about a 45 degree angle relative to the surface of the teeth.

As shown in FIG. 3, the stem 16 of the toothbrush 10 of the present invention is bendable so that the stem 16 and head 12 can be positioned at any fixed position necessary to reach areas of the mouth which are otherwise difficult to reach with a standard toothbrush. To achieve this purpose, the stem 16 may be provided with a centrally located wire 18 of a size and stiffness sufficient to maintain the head 12 and stem 16 configuration selected by the user of the toothbrush 10 while at the same time withstanding the forces applied to the head and stem during brushing. The stem 16 is connected to the handle 20 by snapping the stem 16 in place on the rotating disk 22 preferably with small flexible projections on the bottom of the stem extending through appropriately sized apertures formed in the rotating portion of the rotating disk 22. The flexible projections are dimensioned to snugly fit within the apertures so that the stem is removably secured to the handle when the stem and handle are snapped together. One or more circular indentations 36 are provided at the base of each stem 16 to assist in gripping the stem when it is being connected to the handle 20 via the rotating disk 22.

When a sufficient amount of hand force is applied to rotate the stem, the flexible projections are forced from the present aperture location, and the stem is allowed to rotate until the flexible projections snap into the next aperture, thereby locking the stem in the next angular position relative to the handle. It is clear to those skilled in the art that the position of the aperture or the flexible projections and the number of apertures or flexible projections may be varied to achieve a multitude of desired angular positions. It is also clear to those skilled in the art that a variety of snapping means having projections and apertures may be utilized for the aforementioned function.

As shown in FIGS. 5b–5e, the toothbrush 10 of the present invention includes a plurality of detachable stems 16 with heads 12 of different sizes and shapes containing rows with tufts of bristles 14 variously arranged. In particular, FIG. 5c shows a large oval-shaped head, FIG. 5d shows a small oval-shaped head, FIG. 5e shows a generally rectangular head, and FIG. 5b shows a generally rectangular shaped head wherein the tip to of the head is more narrow than the base of the head in the shape of a truncated triangle. In the preferred embodiment, three of the head designs shown have soft bristles while a fourth toothbrush head has hard bristles which are especially effective for occlusals. When the features of the multiple head arrangements are combined with the flexible positioning capabilities of the stem 16, one obtains a toothbrush 10 which can be adapted to utilize practically all of the head designs and stem angles which are recommended and used by the various toothbrush manufacturers.

As shown in FIG. 5a, the present invention also includes a tubular stem 28 to which a generally U-shaped dental floss holder 26 is attached. The tubular stem 28 of the dental floss holder 26 is tubular in construction so as to accommodate a roll of dental floss therein. A dental floss cutter 38 is attached to or formed in the side of the tubular stem 28. The tubular stem 28 is attached to the handle 20 in the same manner as described above with respect to attachment of the stems 16 which have toothbrush heads 12 with bristles 14.

Use of the toothbrush 10 of the present invention by a right-handed person will now be described. First, the stem 16 having the desired toothbrush head 12 is attached to the rotating disk 22 on top of the handle 20. For this purpose, the stem 16 may include a plurality of small projections or bars on its bottom portion which are shaped to fit into a plurality of grooves formed in the rotation means so that the stem 16 is locked in place by inserting the bars into the grooves and rotating the stem 16 until the stem is locked in place. Next the stem 16 is flexed and formed to the preferred lateral displacement relative to the flat portion of the handle. The toothbrush 10 is then moved into a horizontal position in front of the mouth with the head 12 on the left (bristles 14 facing the mouth) and the handle 20 on the right (flat portion facing mouth). The thumb should be positioned on the flat portion of the handle with the fingers curled around the stem 16. Some of the fingertips may also be positioned on the flat portion of the handle.

Figure 2A:
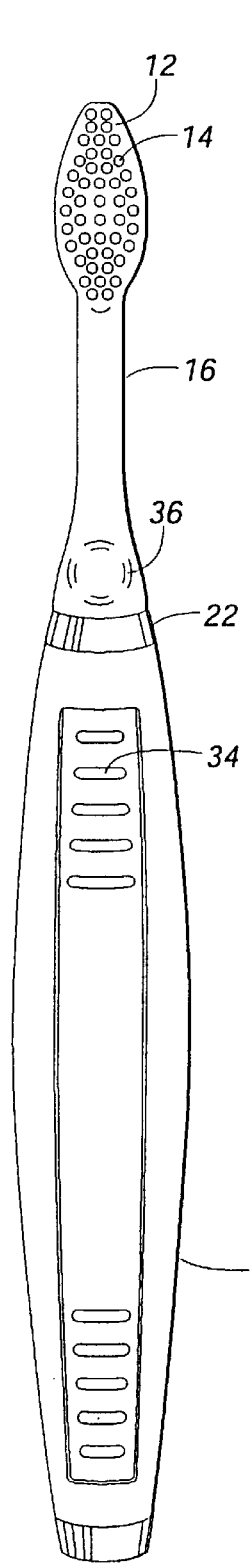
FIG. 2a is a front view of the toothbrush of the present invention demonstrating a standard head orientation.
Figure 2B:
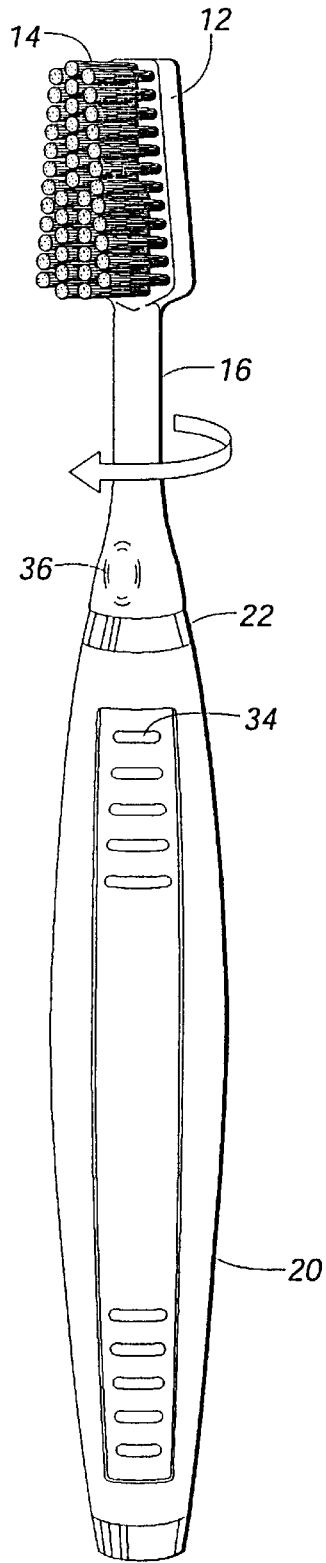
Figure 2C:
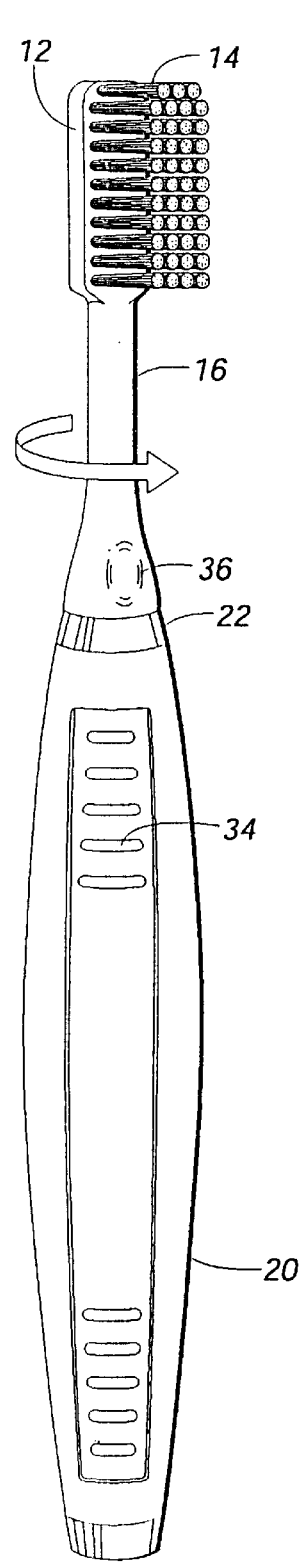
Figure 2D:
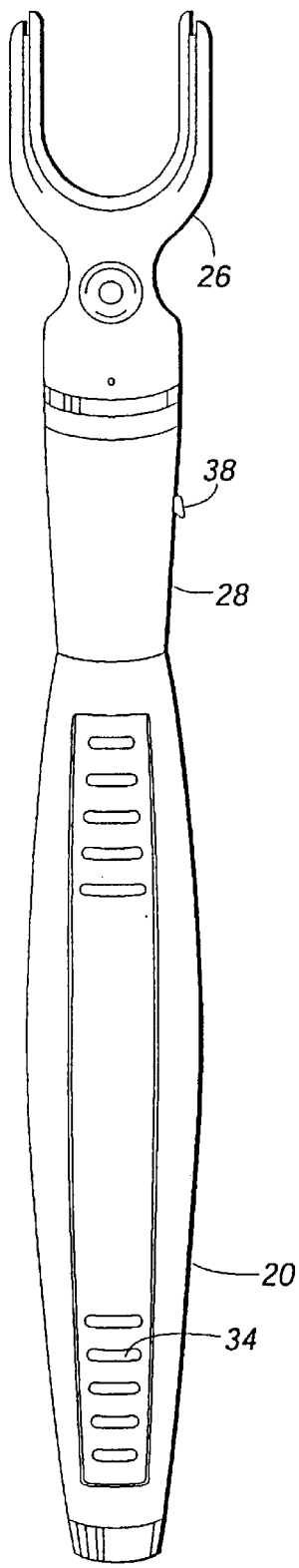
FIG. 2d is a front view of the toothbrush of FIG. 2a with the head replaced with a preferred embodiment of the dental floss holder of the present invention.

To brush the outside surface of the teeth in the upper left quadrant of the mouth, the stem 16 and head 12 are rotated 45 degrees upward (FIG. 2c). The toothbrush 10 is now in position to implement the Bass brushing technique by applying toothpaste to the bristles 14, placing the bristles of the toothbrush against the teeth and gums and using short back and forth strokes as described above. To brush the outside surface of the teeth in the upper right quadrant of the mouth, the same grip is maintained on the handle 20 of the toothbrush. However, the stem 16 and head 12 are rotated so that they are positioned at an upwardly inclined 45 degree angle relative to the outside surface of the teeth (FIG. 2b). When brushing these teeth, the toothbrush is still in a horizontal position in front of the mouth except that the head 12 is now on the right (bristles 14 facing the mouth) and the handle 20 on the left (flat portion facing away from the mouth). Thus, the Bass brushing technique is implemented while using conventional brushing methods without having to contort and angle the hand and wrist into an unnatural position to achieve proper positioning of the head of the toothbrush at a 45 degree angle relative to the front and back surfaces of the teeth. Of course, the dental floss holder 26 may be attached to the handle 20 and the teeth flossed in a conventional manner (FIG. 2d).

In another embodiment of the present invention the stem is only rotatable from a forward facing position defined herein as zero degrees to one of two possible positions, namely forty-five degrees to the left and forty-five degrees to the right (i.e, ±45°). Implementation of the Bass Technique using this embodiment of the present invention is carried out as follows:

A. Grip toothbrush handle normally with thumb on grips and brush lower occlusals.

B. Flip toothbrush completely over and brush upper occlusals.

C. While maintaining same grip rotate stem to far right and brush outer top left quadrant and inner top right quadrant.

D. Again, maintain same grip and rotate stem to far left and brush inner top left quadrant and outer top right quadrant.

E. Simply flip brush completely over and brush outer bottom left quadrant and inner bottom right quadrant.

F. While maintaining same grip, rotate stem to far left and brush outer bottom right quadrant and inner bottom left quadrant.

G. Simply bend stem at any time during brushing for increased comfort and to brush hard-to-reach surfaces.

These instructions only require three very simple (but exact) stem rotations throughout the entire brushing procedure. Because the handle is "double-sided," it enables the user to maintain the same grip throughout the entire mouth. This drastically increases manual dexterity (i.e., effectiveness) and enables the user to be consistent in brushing. The double-sided handle also enables the user to brush all areas of the mouth in the usual or preferred order which aids in compliance and simplicity while using the same natural grip. Furthermore, the double-sided design and three simple rotations not only enables the user to brush normally and naturally but, in addition, drastically increases manual dexterity and comfort. The 45° stem rotation drastically augments a user's understanding of and implementation of the Bass Technique. The instructions for use are simple, requiring only three rotations, and are designed to follow the normal patterns and brushing habits of the average user which is important to implementation of and compliance with the Bass Technique.

With all toothbrushes (even electric toothbrushes) one has to flip the toothbrush over to go from brushing the upper teeth to brushing the lower teeth which, like the toothbrush of the present invention, is normal and natural to all users. However, in order to achieve a 45° angle relative to all dental surfaces, one must constantly change his or her grip (losing dexterity) or, constantly torque the handle and one's hand and wrist to very unnatural grips and positions. Hence, effective brushing using the Bass Technique in all areas of the mouth has been virtually impossible prior to the present invention.

In accordance with another feature of the present invention, FIGS. 6a–6c show an elongated toothbrush head 12 which is bendable so that the user of the toothbrush may adjust the shape or curvature of the head to conform to the contour of specific dental surfaces. For example, the head may be bent forward as shown in FIG. 6c to impart a concave curvature to the bristles 14 mounted in the head so that the bristles more efficiently interact with variations in the convex shape of an individual tooth or the general convex arrangement of one's teeth in the mouth. To facilitate the flexibility of the head while at the same time maintaining sufficient structural integrity to withstand the forces applied to the head during brushing, the head may be formed of rubber with a flexible wire 40 and/or hinges 42 which, along with a flexible substrate 44 to which the tufts of bristles are anchored, are imbedded within the rubber head. As shown in FIG. 6a, the head preferably has an elongated oval design which enables the user of the toothbrush to effectively brush larger areas of the mouth more quickly and effectively. Because the head is longer than the standard toothbrush and is bendable so as to conform to the curvature of one's mouth, effectiveness in brushing is dramatically increased.

Although the present invention has been described with reference to preferred embodiments thereof, it is to be understood that these embodiments are for illustrative purposes and should not be construed as limitations on the scope of the invention. Many modifications are possible. Accordingly, the scope of the present invention should not be determined by the embodiments illustrated, but by the claims appended hereto and their legal equivalents.

We claim:

1. A toothbrush with a bendable head for brushing teeth and gums, said toothbrush comprising:

a generally cylindrical handle, having a longitudinal axis and a cross-section defined by a circular portion for supporting at least one finger and a flat portion for supporting a thumb and fingertips;

rotation means attached to said handle for releasably attaching said handle to a stem, and for selectively positioning said stem at one of a plurality of locations about the longitudinal axis of said handle;

wherein said stem is connected to said rotation means, said stem comprising means for laterally adjusting the position of said stem relative to the longitudinal axis of said handle; and an elongated, rubber head connected to said stem and having a front portion with a plurality of tufts of bristles anchored to a flexible substrate embedded within said rubber head, said front portion being arranged so that in one of said plurality of locations of said rotation means the bristles of the head are at about a forty-five degree angle relative to the surface of said flat portion of said handle, whereby the Bass technique of brushing teeth and gums is implemented by the user of the toothbrush by moving the toothbrush in short strokes against the surface of the teeth and gums in a conventional manner.

2. The toothbrush as recited in claim 1, further comprising a wire embedded within said rubber head to permit modification of the curvature of the head relative to the surface of the teeth when brushing.

3. The toothbrush as recited in claim 2, wherein said wire includes a plurality of hinges spaced along the length of said wire.

4. The toothbrush as recited in claim 1 wherein said handle has a front portion and a back portion, both having a plurality of raised sections attached thereto defining grips.

5. The toothbrush as recited in claim 4 wherein said generally cylindrical handle is about 1 inch in diameter.

6. The toothbrush as recited in claim 1 wherein said rotation means allows selective positioning in about 45 degree increments.

7. The toothbrush as recited in claim 1 wherein said head is generally rectangular in shape.

8. The toothbrush as recited in claim 1 wherein said head is generally oval in shape.

9. The toothbrush as recited in claim 1 wherein said head is generally triangular in shape.

10. The toothbrush as recited in claim 1 wherein said handle is formed of a deformable material which is slightly depressed when a gripping force is applied thereto.

11. The toothbrush as recited in claim 1 wherein said stem may be selectively positioned at an incline relative to the longitudinal axis of said handle.

12. The toothbrush as recited in claim 11 wherein said laterally adjusting means further comprises a centrally located wire.

* * * * *